United States Patent [19]

Vogel

[11] Patent Number: 4,613,219

[45] Date of Patent: Sep. 23, 1986

[54] EYE MOVEMENT RECORDING APPARATUS

[75] Inventor: John D. Vogel, Sagamore Hills, Ohio

[73] Assignee: Burke Marketing Services, Inc., Cincinnati, Ohio

[21] Appl. No.: 586,083

[22] Filed: Mar. 5, 1984

[51] Int. Cl.[4] .............................................. A61B 3/14
[52] U.S. Cl. ..................................... 351/209; 351/210
[58] Field of Search ................................ 351/209, 210

[56] References Cited

U.S. PATENT DOCUMENTS 4,075,657  2/1978  Weinblatt ............................ 351/209
4,145,122  3/1979  Rinard et al. ....................... 351/209

Primary Examiner—Rodney B. Bovernick
Assistant Examiner—P. M. Dzierzynski
Attorney, Agent, or Firm—Wood, Herron & Evans

[57] ABSTRACT

Apparatus for recording eye movement. A light source has its rays directed toward the eye of a subject and a glass dome secured to spectacle frames worn by the subject. The primary and secondary glints reflected off the glass dome and eye cornea, respectively, are transmitted via mirrors, lenses and a fiber optic image guide to a video camera tube. The position of the glints on an XY axis is electronically determined and the information is fed to a computer which compares the data from the two glints and compensates for the head movement which corresponds to movement of the primary glint.

4 Claims, 3 Drawing Figures

EYE MOVEMENT RECORDING APPARATUS

This invention relates to eye movement recording apparatus, and particularly to apparatus which utilizes corneal reflections and compensates for head movement.

At least since the time of the 1958 publication of Mackworth et al, "Eye Fixations Recorded on Changing Visual Scenes by the Television Eye Marker," *Journal of the Optical Society of America*, July, 1958, eye movement has been recorded by reflecting a light source off the cornea and determining the position of the recorded glint, the glint being the reflected beam. This system generally has found use in market research. For example, an advertising print may be projected onto a screen. A subject views the screen and moves his eye to focus on the images on the screen to which the subject is attracted. By recording the eye movement and correlating those movements to the images on the screen, the point of attraction can been determined. As Mackworth points out, head movements can create artifacts or errors. Head movements of as little as 0.075 millimeters will produce an artifact. The solution to head movement commonly practiced has been to provide structure for rigid head fixation.

The structure required for rigid head fixation is at best uncomfortable and not particularly suitable for use with a large number of subjects as would be required for a thorough market research program.

The Whittaker Corporation of Waltham, Mass. has provided apparatus for measuring head movement which does not require total head fixation. In the Whittaker apparatus, the movement of the center of the pupil is compared to the movement of the corneal reflection, the movement of the center of the pupil being a measure of head movement. This information is processed in a digital computer and a scan pattern, with compensation for head movement, is obtained. The disadvantages of the Whittaker system is that it can compensate for only limited head movement as, for example, 2 mm.

An object of the present invention has been to provide improved apparatus which permits the recording of corneal reflections and which compensates for substantially greater head movement than has been possible with prior apparatus.

This objective of the invention is attained by providing a separate reflector mounted on spectacle frames or the like which will move with the subject's head. A light source is directed to the cornea as well as the fixed reflector producing a primary glint from the fixed reflector and a secondary glint from the cornea. The movement of the primary glint is directly related to head movement and the movement of the secondary glint directly related to the movement of the cornea. The glints are transmitted to a television camera tube preferably via an optical fiber light image guide. There, the information is compared and the true location of the subject's gaze is recorded. That information can be portrayed on a screen in the form of a grid overlying the picture on the screen which the subject is viewing or, alternatively, the data can be processed with a printout indicating such information as which image in the picture the subject viewed and how long did the subject spend on the particular image.

The several features of the invention will become more readily apparent from the following description taken in conjunction with the accompanying drawings in which.

Figure 1:
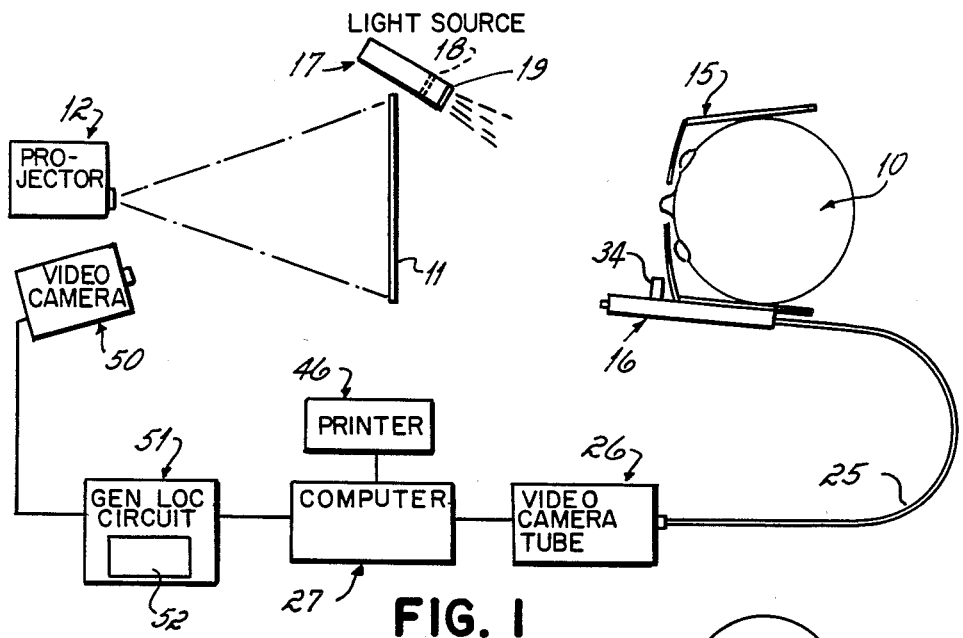
FIG. 1 is a diagrammatic top plan view of the apparatus.

Referring to FIG. 1, the head of the subject is shown at 10 with the subject viewing a picture produced by a projector 12 onto a projector screen 11. Spectacle frames 15 are provided for the subject and a beam receiver 16 is fixed to the spectacle frames. A light source 17 directs a beam of light at the subject so that the rays will impinge upon the cornea of the left eye of the subject as well as a reflector within the receiver 16. The light source includes a filter 18, as, for example, a red filter, which minimizes the disturbance of the light source on the eye of the subject. A dispersing lens 19 is provided to spread the light source and to provide substantially uniform intensity on the cornea and the fixed reflector.

The receiver 16 is connected by a fiber optic image guide 25 to a video camera tube 26. The video camera tube preferably is of high light sensitivity such as is provided by the Ultracon manufactured by RCA. The Raster scan of the video tube will create a voltage spike at the positions of the primary and secondary glints from the fixed reflector and cornea, respectively. This video signal is fed to a computer 27 where it is converted to an analog signal. The analog signal in turn is converted to an XY format corresponding to the positions of the respective glints on XY coordinates. That information is in turn converted to digital information. An eye movement compensation computation is made by the computer in accordance with the following equation:

Horizontal $KH2(Ps - KH1 \times Pp)$ H scale

Vertical $KV2(Ps - KV1 \times Pp)$ V scale

KH2—correction value for horizontal position of the secondary glint.

Ps—position of secondary glint.

KH1—correction value for the horizontal position of the primary glint.

Pp—position of primary glint.

H scale—provides the horizontal direction of the scan +or −1.

V scale—provides the vertical direction of the scan +or −1.

KV2—correction value for the vertical position of the secondary glint.

KV1—correction value for the vertical position of the primary primary glint.

The KH2 and KV2 constants are preferably determined for each subject and correct for variances in the shape of the respective corneas. To obtain the correction value, the subject is asked to look at nine points (3×3) on a television screen as the light source reflects off the cornea of the subject. The position of the reflected glint provides a cursor which moves on the television screen where the nine points are displayed. The amount of deviation of the cursor from the point which the subject is asked to view is automatically fed to the computer and provides the correction value.

Similarly, the KH1 and KV1 are determined. A subject is asked to fix his gaze on a point and to rotate the head. The amount of movement of the cursor which corresponds to the movement of the fixed reflector provides the correction value for the position of the primary glint. This determination need not be made for each subject as an average correction value can be obtained and used in the system.

Figure 2:
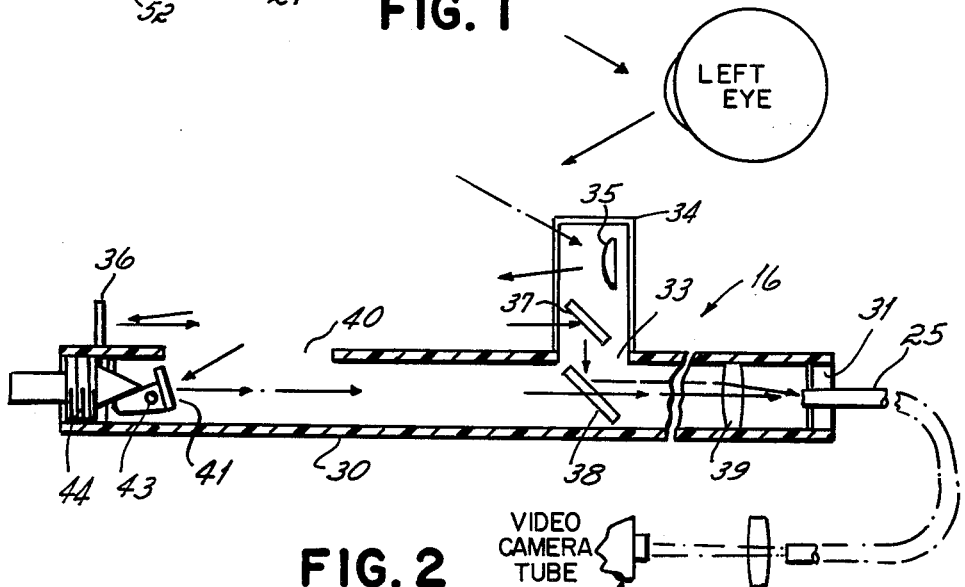
FIG. 2 is a diagrammatic enlarged top plan view of the apparatus partly in section.

The receiver is shown in greater detail in FIG. 2. It includes a tube 30 which is preferably light absorbing as, for example, by being painted black. The tube is connected to the fiber optic image guide 25 at its outlet end 31. The tube has an opening 33 on which a housing 34 is mounted. The housing 34 contains the fixed reflector which is in the form of a glass dome 35. The glass dome has a generally spherical surface which approximates the surface of a cornea. The glass dome cooperates with a first reflector 36, a second reflector 37 and a beam splitter 38 to reflect the primary glint to a lens 39 adjacent the input end of the fiber optic image guide.

The tube has another opening 40 through which the secondary glint from the cornea passes. A single mirror 41 directs the secondary glint through the beam splitter 38 and lens 39 to the fiber optic image guide 25.

The mirror 41 is pivotally mounted on an axis 43 within the tube. It can be rotated slightly by a horizontal screw 44 which engages the mirror 41. The adjustability of the mirror provides a gross adjustment to find the glint when the subject is in place.

A vertical screw engages threads in one end of the tube 30 to raise and lower it so as to provide for a vertical adjustment to "find the glint" when the subject is in place.

A lens 45 is employed to transmit the glint images from the image guide 25 to the video camera tube 26.

Figure 3:
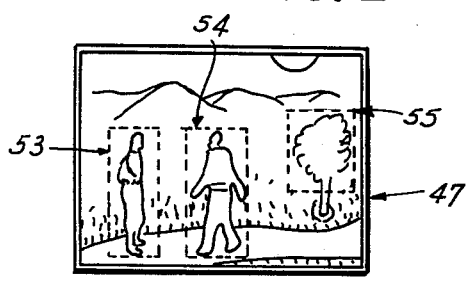
FIG. 3 is a diagrammatic view of a picture viewed by the subject.

The operation of the invention will be described in relation to a market research project involving a print such as is depicted at 47 in FIG. 3. The print will be divided into zones, for example 53, 54 and 55, corresponding to the images within the print. The coordinates of those zones will be entered in the computer. The object will be to determine the percentage of the people who note each zone, the percentage of people who note each zone first and the percentage of people who reexamine any zone.

The subject is first placed before a television screen having the nine positions displayed for the purpose of calibration. The subject is asked to view each point and the deviation of the cursor with respect to each point is entered into the computer for the purpose of satisfying the compensation equation discussed above.

The calibration having been completed, the print is displayed to the subject for a predetermined period of time. As the gaze of the subject moves from point to point, the secondary glint, reflected through the mirrors and image guide, is transmitted to the video camera tube. Similarly, the primary glint which corresponds to any head movement is transmitted to the video camera tube. That data is entered in the computer which provides the compensating computation in accordance with the equations to store the information as to when the gaze fell upon the designated zones of the print and how long the gaze remained in any one zone.

After a preselected number of subjects have viewed the print under substantially identical conditions, the computer will provide a printout to printer 46 setting forth the percentage of people who noted any zone, percentage of people who noted a zone first, and the percentage of people who reexamined a zone.

If desired, a second video camera 50 may be employed and connected to the eye track computer 27 through a gen loc circuit 51. A TV screen 52 can then be used to produce simultaneously the print projected onto the screen 11 as well as the positions of the subject's gaze as it moves about the print. Thus, the eye movement can be visually monitored for demonstration purposes and the like but is not necessary as a part of the regular market research activity.

Having described my invention, I claim:

1. Apparatus for recording eye movement,
    a light source positionable in front of a subject so that light rays can impinge on the cornea of the subject and reflect a secondary glint,
    a receiver for said light rays mountable on the head of the subject, said receiver receiving a secondary glint from a cornea of the subject on which said receiver is mounted,
    a glass dome mounted in said receiver to receive light rays directly from said source, unaffected by reflection from the cornea, and reflect a primary glint from said source off said dome,
    means for transmitting said primary and secondary glints to a video camera tube,
    and means for comparing the positions of said primary and secondary glints to determine eye movement with compensation for head movement.

2. Apparatus as in claim 1 in which said dome has a substantially spherical surface which reflects said light rays.

3. Apparatus as in claim 1 in which said transmitting means comprises
    a fiber optic image guide connecting said receiver to said video camera tube, a lens adjacent the inlet end of said image guide,
    and a system of mirrors transmitting said glints to said lens,
    said mirrors being positioned to provide substantially the same length of beam for each glint.

4. Apparatus as in claim 1 in which said receiver is
    a tube adapted to be mounted on a spectacle frame,
    a fiber optic image guide on one end of said tube and connected to said video camera tube,
    a mirror at the other end of said tube for receiving and reflecting said secondary glint to said image guide,
    said glass dome being mounted intermediate the ends of said tube to receive and reflect said primary glint,
    and a system of mirrors including a beam splitter in said tube through which said secondary glint passes, said system of mirrors reflecting said primary glint to said image guide.

* * * * *